United States Patent
Pearce et al.

(10) Patent No.: US 11,827,009 B2
(45) Date of Patent: Nov. 28, 2023

(54) SCREEN PRINTING APPARATUS AND METHOD

(71) Applicant: Trio Healthcare Ltd, Skipton (GB)

(72) Inventors: Lloyd Pearce, Skipton (GB); Stewart Lee, Skipton (GB)

(73) Assignee: TRIO HEALTHCARE LTD, Skipton (GB)

( * ) Notice: Subject to any disclaimer, the term of this patent is extended or adjusted under 35 U.S.C. 154(b) by 27 days.

(21) Appl. No.: 17/268,057

(22) PCT Filed: Mar. 10, 2020

(86) PCT No.: PCT/GB2020/050566
§ 371 (c)(1),
(2) Date: Feb. 11, 2021

(87) PCT Pub. No.: WO2020/201690
PCT Pub. Date: Oct. 8, 2020

(65) Prior Publication Data
US 2021/0300015 A1 Sep. 30, 2021

(30) Foreign Application Priority Data
Mar. 29, 2019 (GB) .................................. 1904400

(51) Int. Cl.
*B41F 15/34* (2006.01)
*A61L 24/04* (2006.01)

(52) U.S. Cl.
CPC ............ *B41F 15/34* (2013.01); *A61L 24/046* (2013.01); *A61L 2420/02* (2013.01)

(58) Field of Classification Search
CPC .... B41F 15/34; B41F 15/0818; B41F 15/085; B41L 13/02; B41L 13/12; B41M 1/12;
(Continued)

(56) References Cited

U.S. PATENT DOCUMENTS 6,062,135 A    5/2000  Buechele et al.
7,161,056 B2 * 1/2007  Gudnason ........... A61F 13/0283
                                                    602/42
(Continued)

FOREIGN PATENT DOCUMENTS

CN    108755167 A   11/2018
EP      0640492 A1    3/1995
(Continued)

*Primary Examiner* — Matthew G Marini
*Assistant Examiner* — Leo T Hinze
(74) *Attorney, Agent, or Firm* — KIRTON McCONKIE; Evan R. Witt

(57) ABSTRACT

Apparatus and method for the screen printing manufacture of a layer of silicone material. The method and apparatus provide for the deposition of a layer of silicone material having a controllable thickness and shape profile as determined by a template forming part of a screen printing assembly. The present apparatus and method provide a fully controlled automated or semi-automated manufacturing process enabling the deposition of a silicone layer onto a substrate layer serving as a conveyor to transport the silicone layer between different units of the process line including a heating/curing unit, a drying unit and a lamination unit.

20 Claims, 6 Drawing Sheets

(58) Field of Classification Search
CPC .... B41P 2215/50; A61F 5/443; A61L 24/046; A61L 2420/02; A61L 24/0031
See application file for complete search history.

(56) References Cited

U.S. PATENT DOCUMENTS

| | | |
|---|---|---|
| 2010/0152687 A1 | 6/2010 | Carolozzi |
| 2014/0243727 A1* | 8/2014 | Gibas ................. C08K 5/04 602/55 |
| 2015/0182991 A1* | 7/2015 | Binner ................. B41F 15/12 428/189 |
| 2019/0083677 A1* | 3/2019 | Pearce ................. A61L 24/0031 |
| 2019/0282459 A1* | 9/2019 | Boswell ................. A61K 8/42 |

FOREIGN PATENT DOCUMENTS

| | | |
|---|---|---|
| JP | H06-117543 A | 4/1994 |
| KR | 20010025143 A | 4/2001 |
| KR | 20010035918 A | 5/2001 |
| WO | 2013056077 A1 | 4/2013 |
| WO | 2017158340 A1 | 9/2017 |

* cited by examiner

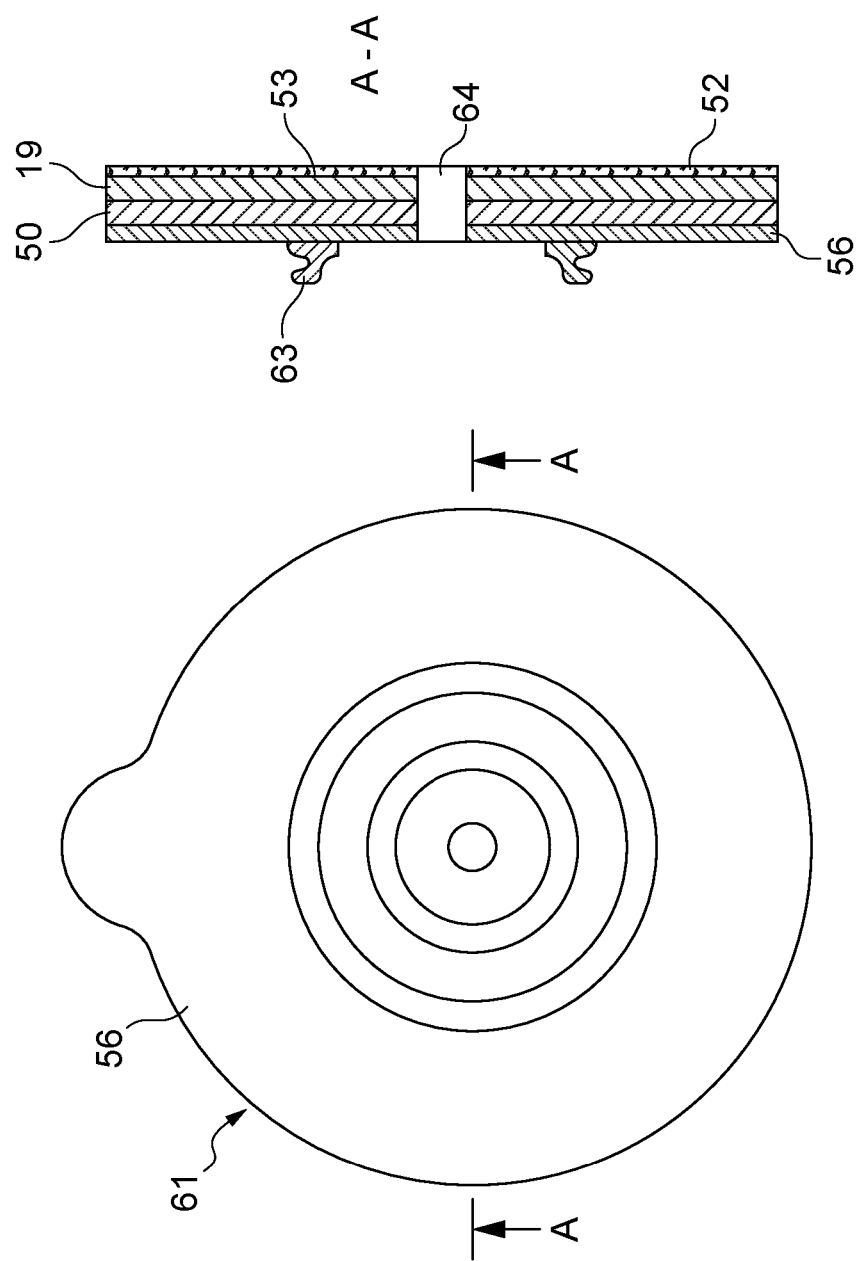

SCREEN PRINTING APPARATUS AND METHOD

FIELD OF INVENTION

The present invention relates to method and apparatus for manufacturing a layer of silicone material and in particular, although not exclusively, to apparatus and method for screen printing silicone material onto a substrate.

BACKGROUND ART

Medical conditions such as ostomy, pressure ulcer, fistula, chronic and acute wounds, highly exuding wounds, and faecal incontinence require management of bodily fluids and waste. Such management is critical to provide wound healing, and to maintain a quality of life in the case of ostomy and faecal incontinence. Devices or appliances used to manage such conditions may be secured to the body using skin adhesives that also find application to secure intravenous or IV fluid lines, and insulin pumps to the body.

In the case of ostomy, a collection bag and an adhesive wafer, (either as separate or combined components) are attached to the peristomal skin through the adhesive wafer to manage stomal waste. It is challenging to securely attach an ostomy device or appliance to an abdominal stoma due to anatomical contour, skin folds or creases, irregular-shaped stomas, surgical scars, etc. While the adhesion of the adhesive has to be securely maintained while the device is in use, at the time of device change or removal, the adhesive should remove from the skin without causing trauma. This balance, between secure adhesion whilst providing non-traumatic removal is critical to the successful management of the medical condition. In order to protect the peristomal skin from stomal effluent, ostomates use adhesive discs such as cohesive seal or moldable ring, which form a dam or gasket around the peristomal skin. These adhesive discs are stretched to fit around the stoma, and pressed down to adhere to the skin. The ostomy wafer or bag is then placed on top of this adhesive gasket. Accordingly, the important characteristics of such adhesive rings include an ability to stretch, with low elasticity, to maintain their shape, to comprise a high tack and adhesion to skin, and also to adhere well to the ostomy appliance.

In the case of wound care, dressings are used to manage the exudate and to promote wound healing. Wounds can occur in any part of the body, and depending on the location, it is often difficult to adhere a dressing to the wound. Similar difficulties also arise in fistula, perianal skin and faecal incontinence management where the anatomy of the body renders it difficult to securely adhere or attach exudate management devices. In negative pressure wound therapy (NPWT) systems used for highly exuding wounds, a vacuum suction is applied to the dressing to displace the exudate from the wound bed and dressing. The securement of such dressings to the peri-wound area is critical to achieve the negative pressure gradient.

There are several commercially available pressure sensitive adhesives (PSA) used as skin adhesives which are based on styrenic block copolymers, polyisobutylene, polyethylene, poly(ethylene-vinyl acetate) (EVA), acrylics, and polyurethane chemistries. PSAs are generally more viscoelastic than elastic. The balance of the elastic-viscoelastic properties renders them to be useful as skin adhesives and to secure devices to the body. Example silicone based skin compatible appliances are disclosed in U.S. Pat. Nos. 8,439,884; 7,842,752; 8,124,675; 8,545,468; WO 2012/003028; U.S. Pat. No. 7,071,268 and US 2013/0096522.

Conventional manufacturing methods for silicone adhesives are typically a multi-stage process in which relatively large layers of a silicone material are cured and then cut and/or punched to the desired shape from the large cured silicone layer. This process is typically wasteful as the already cured silicone material cannot be recycled. This is to be contrasted with the manufacture of alternative hydrocolloid based system. Accordingly, what is required is a method of manufacturing a silicone based skin contactable appliance that addresses these problems.

SUMMARY OF THE INVENTION

It is an objective of the present invention to provide apparatus and method for manufacturing an adhesive skin contactable component and in particular, although not exclusively, to an ostomy coupling component or arrangement configured to exhibit enhanced moisture management when mounted in position at the skin. It is a further objective to provide a manufacturing method and apparatus for a silicone based skin contactable component that is efficient with regard to processing time, materials used and energy consumption.

It is a further specific objective to provide a manufacturing method and apparatus to manufacture thin silicone based material layers typically of the order of 1 mm. It is a further objective to provide a silicone layer material capable of being coupled to or laminated with additional layers of similar or different materials to provide a multi-layer laminate structure.

The objectives are achieved via a screen printing method of manufacture and apparatus in which a liquid or gel phase silicone material may be delivered to a print head and onto a substrate where it may be cured. The method and apparatus include a template onto which the flowable silicone material is delivered to deposit predefined volumes of silicone material onto the substrate of predefined shape such as an annular disk, circular disk and the like. The present method and apparatus are compatible with a variety of different types of polymer material including condensation curable materials and addition curable materials. The present apparatus and method are adapted preferably for two-part addition cured silicone materials having a first part including a vinyl functionalised siloxane polymer and a second part including a silicon hydride containing crosslinker, with the two-parts curable in the presence of a metal catalyst. Optionally, such a silicone polymer material may include a superabsorbent particulate (SAP) and further additives such as permeability modifying polymers and additives to selectively adjust a moisture vapour transmission rate (MVTR) across the silicone layer. Preferably, the present apparatus and method are adapted for processing of thermally cured silicone materials. Optionally, the present apparatus and method may be configured for the processing of radiation curable silicone materials, curable via it or uv radiation.

According to a first aspect of the present invention there is provided a method of manufacturing a layer of a silicone material comprising: delivering the silicone material from a reservoir to a dispensing nozzle at a print head whilst the silicone material is a liquid or flowable gel; dispensing the silicone material onto a template having at least one aperture to allow the silicone material to pass through the template; depositing the silicone material from the aperture onto a substrate; and allowing the silicone material to cure on the substrate as a layer.

Reference within the specification to a 'print head' encompass a fluid dispensing arrangement in which a dispensing nozzle is fed from a reservoir via connection tubing or the like with the print head being movable in a number of different directions and optionally in one, two or three planes.

Reference within the specification to 'a screen or screen assembly' encompass an arrangement adapted to receive a liquid or flowable gel or liquid phase material and to allow deposition of this material from a print head on to a substrate via a screen and template arrangement.

The present method is advantageous to deliver a predefined amount of silicone via the print head onto a screen assembly for subsequent deposition onto a substrate according to a predefined shape and thickness. A pump arrangement, pump or preferably a plurality of gear pumps are operational to control the flow of liquid silicone material from at least one reservoir to a nozzle according to a predefined dose volume and speed. The print head may comprise or carry a wiper blade for wiping the deposited flowable silicone material over the template. Optionally, the wiper blade may be an independent component of the apparatus and controllable independently via at least one actuator such as an electromechanical or hydroelectric actuator.

The present method and aspects therefor is capable of full automatization and electronic control via conventional computer systems, a PCB, microprocessor etc as will be appreciated. The present method and apparatus may be controlled locally or remotely via a suitable communication ports, modules and data transfer components and management systems. The method of manufacturing a layer of the silicone material preferably further comprises spreading the silicone material over the template using a wiper blade. The method may comprise using one or a plurality of wiper blades. The blade together with the print head is capable of controlling a volume and thickness of the printed silicone layer on the substrate. The present method and apparatus is capable of printing silicone based material layers of various thicknesses that may be in the range 100 µm to 2 mm; 100 µm to 1.5 mm; 200 µm to 1500 µm; 500 µm to 1500 µm or 600 µm to 1400 µm.

Optionally, the reservoir comprises a first reservoir and a separate second reservoir, both the first and second reservoirs being connected to a mixing body that is connected to the dispensing nozzle such that the silicone material flows from the first and second reservoirs to the dispensing nozzle via the mixing body. Delivery of the silicone material from the first and second reservoirs is provided by one or a plurality of pumps capable of operation independently so as to control the relative amount of the first and second part silicone material delivered to the print head.

Optionally, the mixing body comprises a static mixer and optionally a helical static mixer in which at least two fluids may be combined and mixed within the mixer body to dispense a homogenous (single phase) liquid or gel. Preferably the mixer is fed directly from the reservoirs via the pumps. Preferably, the silicone material is formed from a first part and a second part stored respectively within the first and second reservoirs. Preferably, the first part comprises a vinyl functionalised siloxane polymer and a catalyst and the second part comprises a silicone hydride containing crosslinker. Optionally, the first and second parts may comprise further components and additives such as a permeability modifying polymer, an MVTR modifying component, an organosilicone resin, an MQ resin, a cohesive strengthening agent and/or a filler.

Preferably, the silicone material is a vulcanised silicone polymer obtained by reacting an alkenyl-substituted polydiorganosiloxane, preferably a polydimethylsiloxane having silicon-bonded vinyl, allyl or hexenyl groups, and an organosiloxane containing silicon-bonded hydrogen atom and a catalyst for the reaction of the SiH groups with the Si-alkenyl (SiVi) groups, such as a platinum metal or its compounds or its complexes thereof. The ratio of SiVi:SiH can be 10:1 to 1:10. Preferred ratio of SiVi:SiH is 1:1. Altering the ratio of the reacting silicones from 1:1 ratio can change the adhesive properties of the layer. If a firmer, lower tack gel is required, the SiH component is higher than SiVi, and if a softer layer with higher tack is required, the SiVi component may be higher than SiH. The silicone compositions may be cured at ambient temperatures, but curing times can be reduced by exposure to elevated temperatures, from about 40° C. to about 150° C. Non-limiting examples of such silicone polymer precursors include Soft Skin Adhesives SSA MG-7-1010, SSA 7-9900, 7-9950 from Dow Corning Corporation, Silpuran® 2114, 2117, 2122, 2130, 2140, 2142 and combinations thereof, SilGel® 612 from Wacker Chemicals. Hydrophilic group containing silicones, according to the present disclosure, may contain polar groups such as acid, amido, amino, sulfonyl, carboxyl, phosphate, phosphonate, etc., on the polydimethylsiloxane backbone. These groups could be present in an ionic form.

Preferably, an organosilicone resin is included in the first or second part prior to addition curing. Preferably, the organosilicone resin is an MQ resin. The organosilicone resin and in particular the MQ resin is advantageous to provide the desired balance between adhesive tack and peel/release characteristics. Optionally, the MQ resin has at least one reactive group such as hydroxyl, alkoxy, hydride, or vinyl functionalities. The silicone resin may comprise a cage-like oligosiloxane with the general formula of $R_nSiX_mO_y$, where R is a non-reactive substituent, usually Me or Ph, and X is a functional group H, OH, vinyl, or OR. These groups are further condensed to enhance or contribute to the resulting crosslinked polysiloxane network. Non-limiting examples of commercially available MQ resins are MQ-RESIN POWDER 803 TF from Wacker Chemical Corporation; VQM-135, VQM-146, HQM-105, HQM-107, SQO-299, and SQD-255 from Gelest Inc., Prosil 9932, MQOH-7 from SiVance, LLC.

Preferably, a cohesive strengthening agent is including in the first part or the second part prior to addition curing. Optionally, the cohesive strengthening agent comprises any one or a combination of the set of: fumed silica, fumed alumina, colloidal silica, nanoclays, silicates, silane treated organic polymers, polymeric metal oxides, and non-polymeric metal oxides. Preferably, the cohesive strengthening agent comprises fumed silica. The strengthening agent contributes to the cohesive strength characteristics of the component and assists with maintaining integrity of the silicone adhesive layer in response to moisture absorption by the SAP and the moisture-vapour transition management of the permeability modifying polymer additive. In particular, the cohesive strengthening agent is further advantageous to minimise and eliminate layer residue once released from the skin. The strengthening agent is further advantageous to facilitate distribution of the SAP and the permeability modifying polymer additive within the matrix. Furthermore, the cohesive strengthening agent further improves the integrity and cohesive strength at the perimeter edge of the silicone layer so as to reduce 'edge bleed'. Non-limiting examples of cohesive strengthening agents of the present disclosure include silica, which could be fumed or precipitated silica such as AEROSIL® and SIPERNAT® grades, respectively, from Evonik Industries. The silica powders could be hydrophilic or hydrophobic, such as AEROSIL® 300, AEROSIL® 255, AEROSIL® R 812, AEROSIL® R 812 S, SIPERNAT® 120, SIPERNAT® 218, etc. Other non-limiting examples of cohesive strengthening agents include fumed alumina, colloidal silica, nanoclays, silicates, silane treated organic polymers, polymeric metal oxides, non-polymeric metal oxides, and the like.

Preferably, the method comprises delivering the first and second parts to the mixing body at a temperature below a curing temperature of the silicone material. Optionally, the method comprises delivering, dispensing and depositing the silicone material onto the substrate at around room temperature (i.e. in a range 20 to 25° C. or more preferably 20 to 22° C.). The curing temperature or gel temperature of the silicone material may in a range 110 to 120° C. Curing/vulcanisation of the present silicone material may vary depending upon relative concentrations and components within the first and second parts.

Preferably, the step of allowing the silicone material to pass through the aperture comprises passing the silicone material through a mesh screen extending across the aperture.

Optionally, a hole or opening size of the mesh screen may be in a range 200 to 1500 µm; 300 to 1400 µm; 400 to 1300 µm; 500 to 1200 µm; 600 to 1000 µm; 700 to 1000 µm; 800 to 900 µm. The hole or opening size refers to a maximum width, length or diameter of each aperture of the mesh as defined by the thread of the mesh i.e., the warps and wefts. Such sizes would be suitable to support and prevent passage of particles, beads or spheres of 1000 µm diameter.

Optionally, the mesh comprises a size 12/140, there being 140 threads per linear inch (55 threads per linear cm) in both x and y directions (wefts and warps). Optionally, the mesh comprises a size in the range 20 to 100, 30 to 90, 30 to 80, 30 to 70 or 40 to 60 threads per linear cm in both x and y directions (wefts and warps). Optionally, a density of the mesh screen may be in a range 20 to 100 T, 30 to 90 T, 30 to 80 T, 30 to 70 T or 40 to 60 T where reference to mesh includes the 'threads per centimetre'.

Such sizes would be suitable to support and prevent passage of particles, beads or spheres of 1000 µm diameter.

Preferably, the mesh screen comprises a metal material. Optionally, the mesh screen may comprise a polymer material. Preferably, the mesh screen may be mounted to and/or surrounded by a solid plate such that the silicone material is configured to flow through the mesh and not through the surrounding plate.

Preferably, the silicone material is delivered to and dispensed from the nozzle in predefined dose volumes. Optionally, the predefined dose may comprise volumes of in a range 5 to 50 cm³, 5 to 45 cm³ or 5 to 40 cm³.

Optionally, the method may comprise raising and lowering the template and the screen relative to the substrate between the dispensing of the silicone material onto the template from the nozzle. The template and the screen may be mounted at a screen assembly movably controlled by one or a plurality of actuators such as electromechanical or electrohydraulic actuators. The screen assembly encompassing the template and the screen is capable of being raised and lowered vertically between printing operations in which the silicone material is deposited onto the substrate.

Preferably, the method comprises conveying the silicone material deposited on the substrate linearly from a position under the print head once the template has been raised relative to the substrate. Preferably, the method further comprises maintaining the substrate substantially stationary under the print head whilst the silicone material is dispensed onto the template and allowed to pass through the aperture.

The method preferably further comprises heating the silicone material on the substrate to a temperature at or above a curing temperature of the silicone material. The heating step may be undertaken within a flatbed heater, oven or heating jacket into which the substrate is capable of being transported. Preferably, the substrate is transported into the heating jacket/oven as a conveyor belt arrangement in which the substrate extends between a pair of rollers (including a substrate dispensing roller and substrate collecting roller). A suitable tensioning device may be applied to the substrate at or between the rollers. Accordingly, the heating jacket or oven is configured to surround at least a portion of the substrate extending between the rollers. The heating oven or jacket is preferably thermostatically controlled locally or remotely and may comprise a flat bed drier. Suitable control apparatus is provided to maintain the substrate stationary within the heating jacket or oven for a predetermined time period to provide curing of the silicone material to transition from a liquid or gel phase to a solidified gel, rubber or solid phase. Optionally, the method comprises maintaining the silicone material above the gel temperature for a curing time period in a range 30 seconds to 10 minutes; 1 minute to 8 minutes; 1 minute to 6 minutes; 2 minutes to 5 minutes or 2 minutes to 4 minutes.

Optionally, the method may further comprise drying the cured silicone material within a dryer at a temperature below the curing temperature and above 20° C. for a drying time period. Optionally, the drying step may comprise using a horizontal dryer or a tower dryer in which the substrate is transported substantially vertically (in a vertical plane) around a set of rollers within a housing. Preferably, the tower dryer is thermostatically controlled as described with reference to the heating oven.

Optionally, after the step of drying the silicone material the method comprises creating a tension in the substrate using a tensioning device. Preferably, after the step of tensioning the substrate, the method comprises applying a release liner to an exposed surface of the silicone material positioned on the substrate. Preferably, the method further comprises after the step of tensioning the substrate, applying a support layer to an exposed surface of the substrate opposite to a surface in contact with the silicone material.

According to a second aspect of the present invention there is provided an apparatus to manufacture a layer of silicone material comprising: at least one reservoir to store at least a part of the silicone material in a liquid or gel phase; a fluid dispensing nozzle positioned at a print head and connected to the reservoir for dispensing the silicone material; a template having at least one aperture to allow the silicone material to flow through the template; and a substrate positionable to receive the silicone material from the aperture of the template.

Preferably, the substrate is provided at or is a part of a conveyor arrangement to enable the substrate to move linearly relative to the print head. Reference within this specification to the substrate configured to move linearly relative to the print head encompasses a conveyor belt arrangement in which the substrate is provided as the belt linearly drivable between a supply (or source) unit of the substrate such as a roll of the substrate and a collection unit optionally in the form of a roll onto which the substrate is conveyed from a supply roll. Optionally, one or both the first and second rolls may be drivable using a motor that may preferably be electronically controlled with regard to speed and torque. Such arrangements may comprise an integral tensioning arrangement to maintain tension within the substrate to carry the deposited silicone material in a horizontal orientation prior to curing.

Preferably, the apparatus comprises an actuating mechanism to raise and lower the print head relative to the substrate. The actuating mechanism may comprise suitable electronic, mechanical or hydraulic actuators being electronically and/or controlled locally or remotely via a PC, personal digital assistant (PDA), microprocessor, PCB and/or the like.

Preferably, the at least one reservoir comprises a first reservoir and a second reservoir each connected to a mixing body, the mixing body connected to the dispensing nozzle. The first and second reservoirs may comprise containers, drums or vessels connected to the print head via hosing or other suitable conduits to allow fluid flow. The reservoirs may be provided with suitable pumps controllable independently. Preferably, the apparatus comprises a first pump coupled to the first reservoir and a second pump coupled to the second reservoir to control a delivery speed and/or volume of the silicone material to the nozzle. Preferably the pumps are gear pumps.

Optionally, the first reservoir comprises a first part of silicone material and the second reservoir comprises a second part of the silicone material, the first and second parts combinable and curable to form the silicone layer on the substrate. Preferably, the first part comprises a silicone polymer and a catalyst and the second part comprises a silicone polymer (comprising a silicon hydride) and a cross-linker. The first or second part may comprise a moisture control particulate such as a superabsorbent particle including for example a polyacrylate. The first or second part may further comprise a silanol resin such as an MQ resin. The first and second part may further comprise a cohesive strengthening agent such as fumed silica.

Preferably, the apparatus comprises a conveyor arrangement formed from the substrate in which the conveyor arrangement comprises a first supply roll of the substrate and a spatially separated second collecting roll of the substrate; and drive means coupled to at least the first or second roll wherein a linear section of the substrate extends between the first and second rolls and the print head and the template are positioned adjacent a region of the linear section.

Preferably, the apparatus comprises a heater unit to heat the silicone material deposited on the substrate to a temperature at or above a curing and/or gel temperature of the silicone material.

Preferably, the apparatus comprises a mesh screen extending across the at least one aperture. The mesh screen is effective to allow the through-flow of the silicone material but prevent undesirable 'flooding' of the substrate and loss of the predefined and desired shape profile of the deposited silicon layer resulting from and as determined by the template aperture(s). Optionally, a hole or opening size of the mesh screen is in a range 200 to 1500 µm; 300 to 1400 µm; 400 to 1300 µm; 500 to 1200 µm; 600 to 1000 µm; 700 to 1000 µm; 800 to 900 µm. Such a configuration has been found to provide the desired flow control of the pre-cured silicon material having a viscosity of 1,000 to 80,000 mPa·s at around room temperature as measured using standard cone and plate viscosity testing such as International Standards BS EN ISO/IEC 17025 and ISO 17034.

According to a further aspect of the present invention there is provided a silicone layer, disk, flange, annular gasket, wafer or ring manufactured by the method and apparatus as described herein.

According to a further aspect of the present invention there is provided a skin compatible component attachable to mammalian skin comprising a silicone material layer manufactured by the method and apparatus as described herein. The component may form part of an ostomy coupling device and in particular a skin compatible component of an ostomy coupling device.

BRIEF DESCRIPTION OF DRAWINGS

A specific implementation of the present invention will now be described, by way of example only, and with reference to the accompanying drawings in which:

FIG. 6A is a plan view of an ostomy appliance coupling according to a specific implementation of the present invention;

FIG. 6B is a cross section through A-A of the ostomy coupling of FIG. 1.

DETAILED DESCRIPTION OF PREFERRED EMBODIMENT OF THE INVENTION

Apparatus and method are provided for the automated or semi-automated manufacture of a layer of silicone material being controllable to achieve relatively thin and uniform layer thicknesses of the order of 1000 µm or less and optionally 200 µm to 1500 µm. The present method utilises screen printing in which the silicone material in a flowable state is delivered onto a substrate that forms a conveyor assembly in which the silicone material is cured on the substrate as a continuous automated or semi-automated process.

Figure 1:
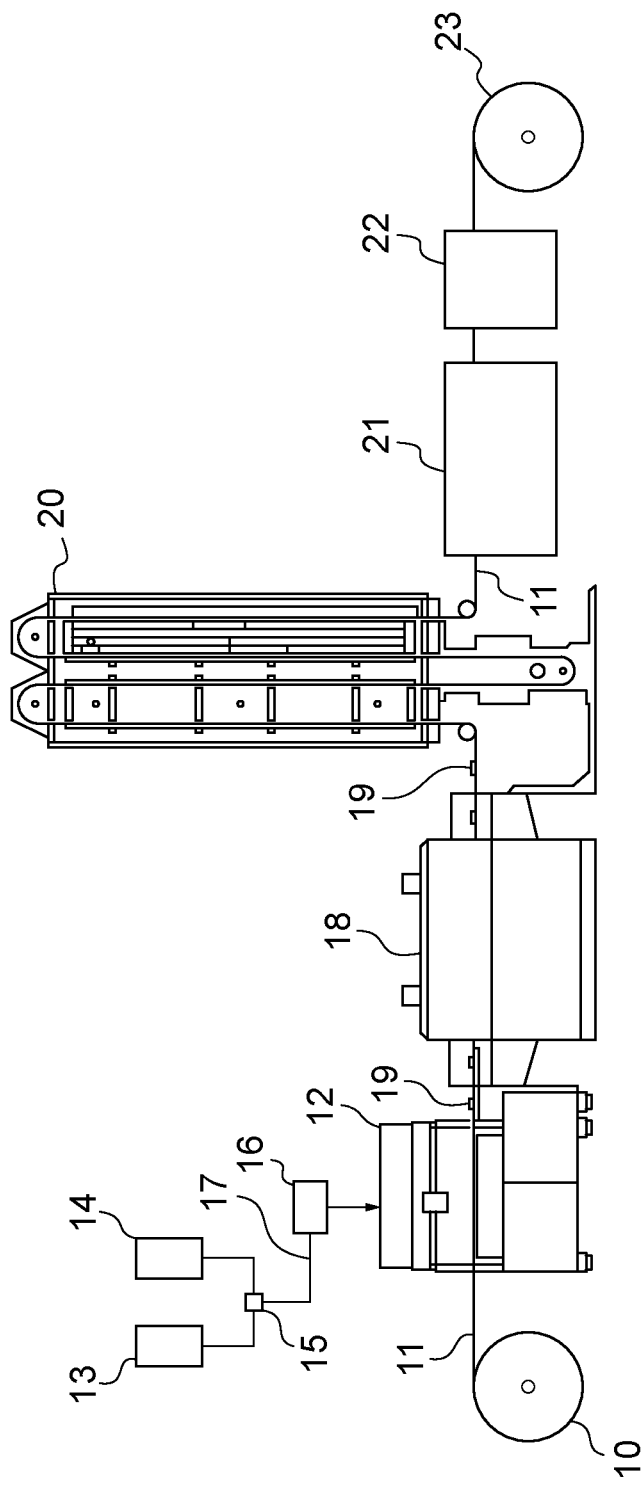
FIG. 1 is a side elevation view of screen printing apparatus for the manufacture of a silicone material layer via a screen printing process.

Referring to FIG. 1, the screen printing apparatus comprises a source roll 10 of a substrate material being a polyurethane (PU) film provided on a paper carrier. The PU film and paper carrier are drawn from source roll 10 to a collection roll indicated schematically by reference 23 at an end point of the present apparatus. The PU film and paper carrier are tensioned between the rolls 10, 23 to provide a taut webbing substrate (film) 11 extending through the various stations of the present apparatus and between the rolls 10 and 23.

Figure 2:
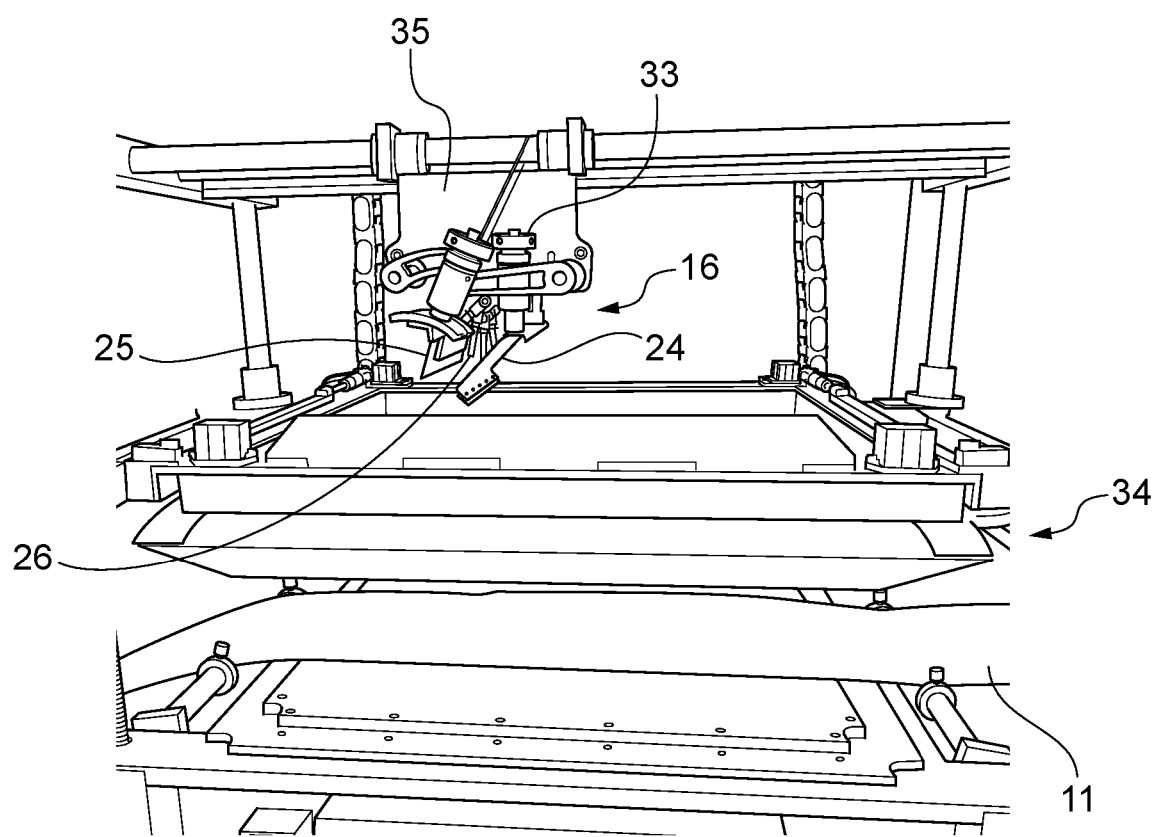
FIG. 2 is a perspective view of a print head and a print station according to a specific implementation of the present invention.
Figure 3:
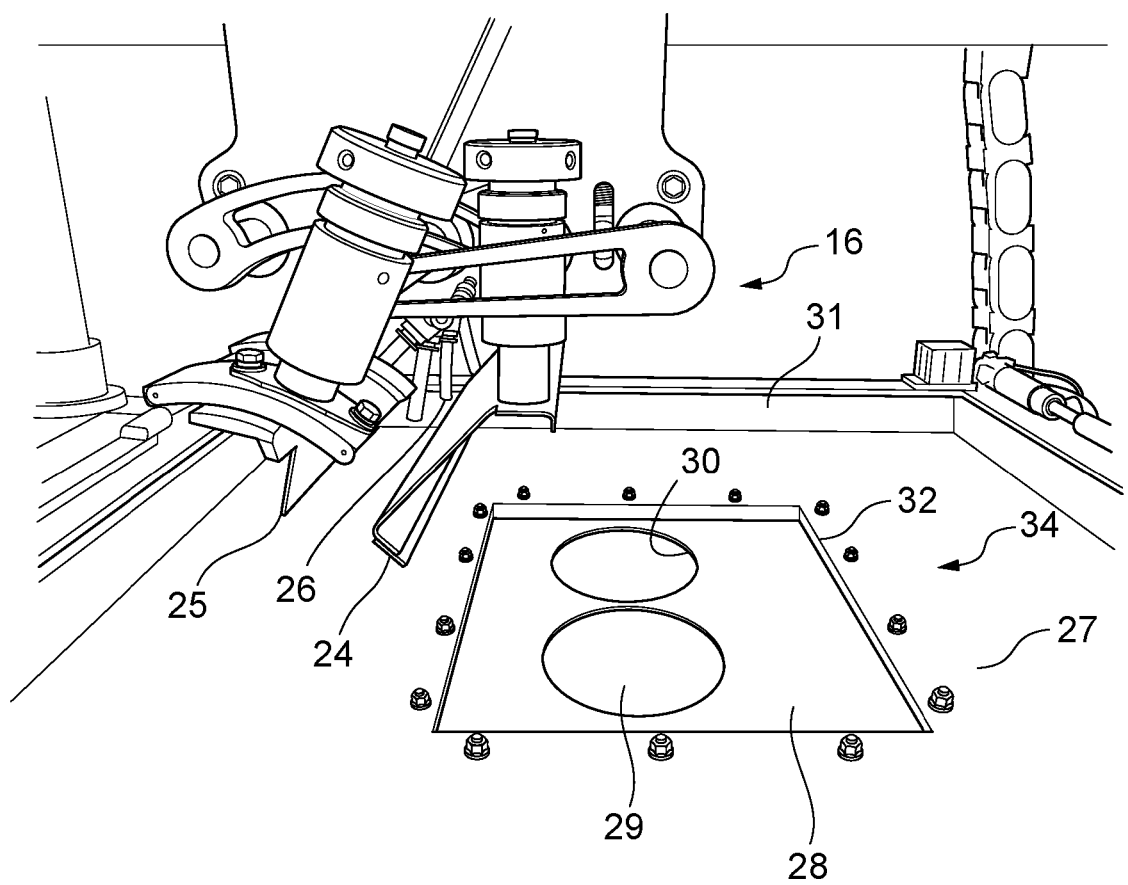
FIG. 3 is a further perspective view of the print head and print station of FIG. 2.

The apparatus comprises a screen printing station 12. Referring to FIGS. 2 and 3, the printing station 12 comprises a print head 16 and a screen assembly 34 positioned in a vertical plane between the print head 16 and taut PU film 11. Print head 16 comprises an inclined plate 24 extending from a lower region of a print head body 33. A blade 25 also extends from an underside of print head body 33 opposed to a lower region of inclined plate 24. A nozzle 26 extends downwardly from body 33 having a dispensing end positioned opposed to inclined plate 24. Print head 16 is provided at a mechanical actuator mount unit 35 adapted to move print head 16 backwards and forwards in a generally horizontal plane relative to screen assembly 34.

Referring to FIG. 3, screen assembly 34 comprises a frame 31 that mounts within its perimeter a solid base plate 27 having a central aperture 32. A generally plate like template 28 is mounted within aperture 32. Template 28 comprises a pair of circular apertures 30. A mesh screen 29 extends across and underside of template 28. Print head 16 is mounted directly above template 28 such that a flow of silicone material is capable of being dispensed from nozzle 26 to flow down inclined plate 24 onto template 28 so as to flood the template 28 at the region of the aperture 32. As head 16 is adapted to traverse in a horizontal plane backwards and forwards over plate 27, blade 25 is adapted to wipe the silicone material over template 28 and across mesh screen 29 extending across template apertures 30.

Referring again to FIG. 1, the apparatus further comprises a first and second reservoir 13, 14 containing respectively a first and a second part of a silicone formulation being a two-part addition curable silicone formulation. A respective gear pump (not shown) is coupled to each respective reservoir 13, 14 to control a volume and speed of each silicone part pumped from each reservoir 13, 14 to a static mixer 15 via a conduit network 17. Static mixer 15 is formed from an Archimedes type screw mixer. The homogenous mixed silicone formulation is then supplied to the print head 16 via suitable tubing (17) to be delivered onto the template 28 and mesh screen 29 exposed via template apertures 30. PU film 11 is fed through the screen printing station 12 to pass directly underneath template 28 and mesh screen 29. The pre-cured formulation is deposited by print head 16 through screen assembly 34 and onto the PU film 11 as deposited silicone layers 19.

A flat bed dryer 18 is positioned in the conveying direction downstream of the screen printing station 12 to receive the pre-cured silicone layers 19 deposited on PU film 11. Dryer 18 is thermostatically controlled to a temperature in a range 110 to 120° C. corresponding to the curing and/or gel temperature of the silicone formulation. A drive motor is coupled to one or both of the rolls 10, 23 so as to control a speed by which silicone layers 19 are passed through flatbed dryer 18. Optionally, the deposited silicone layers 19 may be stationary for a predetermined time period within dryer unit 18. Typically, the layers of silicone 19 may be maintained within dryer 18 for 2 to 4 minutes.

A tower dryer 20 is positioned downstream of flatbed dryer 18 to receive the cured or partially cured silicone layers 19 adhered to the PU film 11. A 'nip out-feed' and tensioner unit 21 is positioned in a conveying direction downstream of tower dryer 20 to receive the fully cured and dry silicone layers 19 on PU film 11. A lamination station 22 is positioned in a conveying direction downstream of the nip out-feed web tensioner unit 21. Lamination station 22 may comprise or be fed by rolls of additional material to be laminated with the PU film 11 and silicone layers 19 as described referring to FIGS. 5A to 5C to create a multilayer laminate structure. The resulting laminate may then be further processed according to supplementary downstream procedures that may include cutting, trimming, stamping or punching operations.

Figure 4:
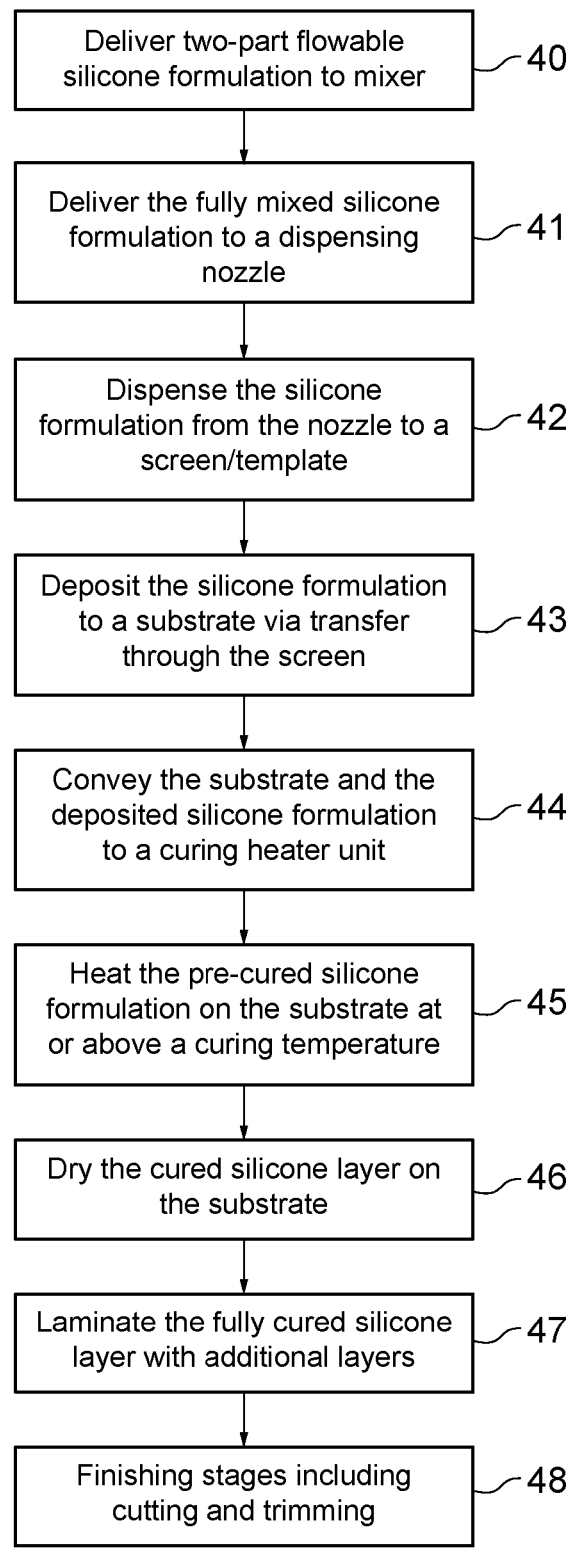
FIG. 4 is a flow diagram of the screen printing process according to one aspect of the present invention.

An overview of the manufacturing process is described referring to FIG. 4 in which the two-part flowable silicone formulation is initially delivered from reservoirs 13, 14 to the static mixer 15 at stage 40. The homogenous silicone material is then fed to the print head 16 from the static mixer 15 at stage 41. The flowable silicone formulation is then deposited from nozzle 26 onto the template 28 and screen 29 within the screen printing station 12 at stage 42. The silicone material is then forced through mesh 29 via wiper blade 25 traversing to and fro over template 28 to be deposited onto the underlying PU substrate 11 at stage 43. The size of the mesh screen 29 is configured specifically to control a rate of flow of the silicone material from the template 28 to the underlying PU substrate 11. According to the specific implementation, mesh screen 29 comprise an opening size in a range 600 to 1000 µm. Such an arrangement provides an appropriate balance between sufficient through-flow and the need to avoid flooding of the PU substrate by the silicone material that would otherwise destroy the predetermined deposition shape corresponding to the template apertures 30.

The deposited silicone layers 19 are then conveyed via the PU substrate 11 to the flatbed dryer at stage 44. The silicone layers 19 are then heated at around their gel point (110 to 120° C.) for a predetermined time at stage 45. The cured or partially cured silicone layers 19 are then dried (via a tower dryer 20) at stage 46 before being fed to the nip out-feed web tensioner unit 21. The silicone layers and PU layer are then laminated at stage 47 within the lamination station 22 to create a multi-layer laminate structure at stage 47. Optionally, the resulting structure may then be finished according to various downstream finishing processes such as cutting and trimming at stage 48 before or after collection on roll 23 at stage 48.

Figure 5A:
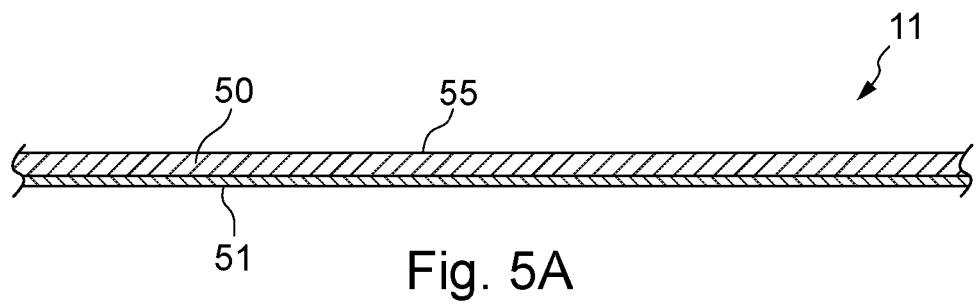
FIG. 5A is a cross section through a substrate to form a conveyor assembly to receive the silicone material.
Figure 5B:
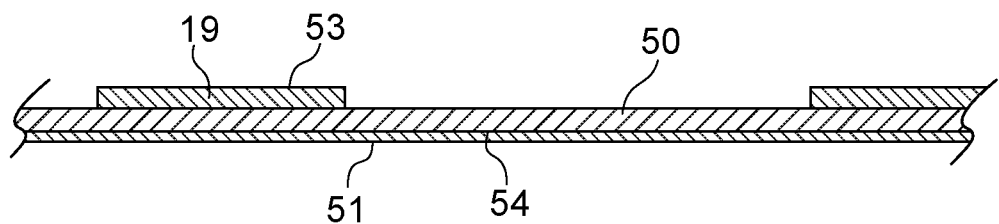
FIG. 5B is a cross section of the substrate of FIG. 5A including the silicone material deposited on an upper surface of the substrate.
Figure 5C:
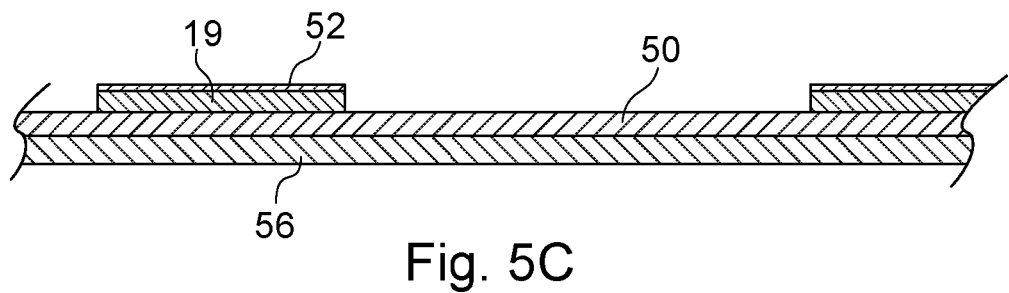
FIG. 5C is a cross section through the substrate of FIG. 5B including the silicone material laminated with additional layers.

Referring to FIGS. 5A to 5C, PU film 11 according to one embodiment includes an elongate sheet of polyurethane (PU) 50 having an exposed upward facing surface 55. A sheet of a carrier paper 51 is adhered to an underside surface 54 of the PU layer 50. Paper carrier layer 51 may be removed at any position within the apparatus of FIG. 1 but is conveniently removed during or prior to the processing at lamination station 22. As illustrated in FIG. 5B, the silicone material deposited on surface 55 of PU layer 50 as circular layers/disks of silicone material 19. Each silicone layer comprises a corresponding upward facing surface 53. Referring to FIG. 5C, after exiting lamination station 22, the fully assembled composite structure comprises a silicone layer 19 having a release liner layer 52 attached to the exposed silicone surface 53 and a polyethylene (PE) secondary substrate 56 layer attached to the underside surface 54 of PU layer 50 (in place of the carrier paper layer 51). As will be appreciated, the paper carrier layer 51 is removed from surface 54 prior to lamination with the PE secondary substrate 56. The four layer structure is then cut and trimmed to create a multilayer laminate disk as illustrated in FIGS. 6A and 6B where FIG. 6B is a cross section through A-A of FIG. 6A. The multilayer structure 61 of FIGS. 6A and 6B is specifically adapted as a skin contactable ostomy coupling in which silicone layer 19 is adapted for positioning in direct contact with the peri-stomal skin surrounding a stoma. The multilayer structure is provided with a central aperture 64 for alignment and interfacing with the stoma. As illustrated, each of the layers 52, 19, 50 and 56 are annular having a generally circular disk-like shape profile with central aperture 64 provided though all or most of the layers.

According to the specific implementation, silicone layer 19 comprises a thickness in a range 100 to 1500 µm, PU layer 50 comprises a thickness in a range 20 to 50 µm and PE substrate layer 56 comprises a thickness in a range 80 to 150 µm with a release liner layer 52 having a thickness in a range 100 to 250 µm. PE layer 56 may be secured to PU layer 50 via heat treatment, ultrasonic welding or via an adhesive. PE layer 56 provides a mount for a first part 63 of an ostomy appliance coupling mechanism (not shown) to releasably engage with a second part of a coupling mechanism provided at an ostomy appliance, in particular an ostomy bag. The first part 63 is preferably formed as an annular flange capable of frictionally integrating and releasably locking with the coupling mechanism second part so as to provide a sealed coupling between an ostomy bag (not shown) and the multilayer structure 61. Release liner 52 may comprise a low density polyethylene (LDPE) of thickness 100 to 250 μm positioned over silicone layer surface 53 and capable of being removed conveniently prior to mounting of the structure 61 into contact with the skin of a person via silicone surface 53.

The invention claimed is:

1. A method of manufacturing a skin contactable multilayer component having a silicone material comprising the steps of:
    delivering the silicone material from a reservoir to a dispensing nozzle at a print head whilst the silicone material is a liquid or flowable gel;
    wherein the reservoir comprises a first reservoir and a separate second reservoir, both the first and second reservoirs being connected to a mixing body that is connected to the dispensing nozzle such that the silicone material flows from the first and second reservoirs to the dispensing nozzle via the mixing body, wherein the silicone material is formed from a first part comprising a vinyl siloxane polymer and a second part comprising a silicone hydride (Si—H) containing crosslinker, the first part and a second part stored respectively within the first and second reservoirs;
    dispensing the silicone material onto a template having at least one aperture to allow the silicone material to pass through the template, the silicone material being delivered to and dispensed from the nozzle in a predefined dose volume;
    spreading the silicone material over the template using a wiper blade to deposit the silicone material from the aperture onto a substrate and maintaining the substrate substantially stationary under the print head when the silicone material is dispensed onto the template and allowed to pass through the aperture, the substrate being a conveyor belt arrangement in which the substrate is provided as the belt linearly drivable between a supply or source unit of the substrate and a collection unit to enable the substrate to move linearly relative to the print head;
    conveying the silicone material deposited on the substrate linearly from a position under the print head to a heating jacket/oven; and
    heating the silicone material on the substrate at the heating jacket/oven to a temperature at or above a curing temperature of the silicone material, thereby curing and adhering the silicone material to the substrate to form the skin contactable multilayer component comprising a layer of the silicone material and the substrate; and
    cutting, trimming, stamping or punching the adhesive skin contactable multilayer component including the layer of the silicone material and the substrate.

2. The method as claimed in claim 1 wherein the step of allowing the silicone material to pass through the aperture comprises passing the silicone material through a mesh screen extending across the aperture.

3. The method as claimed in claim 2 wherein a size of the mesh screen is in the range 20 to 100 threads per linear cm in both x and y directions.

4. The method as claimed in claim 2 comprising raising and lowering the template and the screen relative to the substrate between the dispensing of the silicone material onto the template from the nozzle.

5. The method as claimed in claim 4 further comprising conveying the silicone material deposited on the substrate linearly from a position under the print head once the template has been raised relative to the substrate.

6. The method as claimed in claim 2 wherein a size of the mesh screen is in the range 30 to 90 threads per linear cm in both x and y directions.

7. The method as claimed in claim 2 wherein a size of the mesh screen is in the range to 80 threads per linear cm in both x and y directions.

8. The method as claimed in claim 2 wherein a size of the mesh screen is in the range 30 to 70 threads per linear cm in both x and y directions.

9. The method as claimed in claim 2 wherein a size of the mesh screen is in the range 40 to 60 threads per linear cm in both x and y directions.

10. The method as claimed in claim 1 comprising maintaining the silicone material above the curing temperature for a curing time period in a range 30 seconds to 5 minutes.

11. The method as claimed in claim 1 further comprising drying the cured silicone material within a dryer at a temperature below the curing temperature and above 20° C. for a drying time period.

12. The method as claimed in claim 11 wherein after the step of drying the silicone material creating a tension in the substrate using a tensioning device.

13. The method as claimed in claim 12 wherein after the step of tensioning the substrate, applying a release liner to an exposed surface of the silicone material positioned on the substrate.

14. The method as claimed in claim 13 further comprising after the step of tensioning the substrate, applying a support layer to an exposed surface of the substrate opposite to a surface in contact with the silicone material.

15. The method as claimed in 1 wherein the substrate is a polyurethane (PU) film and the method further comprising prior to the step of cutting, trimming, stamping or punching:
    attaching or laminating a release liner layer to an exposed surface of the silicone layer; and
    attaching or laminating a polyethylene (PE) secondary substrate layer to an underside surface of PU film;
    to form the adhesive skin contactable multilayer component.

16. The method as claimed in claim 1 wherein the conveyor belt arrangement is formed from the substrate that extends between a pair of rollers including a substrate dispensing roller and substrate collecting roller.

17. The method as claimed in claim 16 wherein the heating jacket/oven is configured to surround at least a portion of the substrate extending between the rollers.

18. The method as claimed in claim 1 comprising maintaining the silicone material above the curing temperature for a curing time period in a range 1 minute to 5 minutes.

19. The method as claimed in claim 1 comprising maintaining the silicone material above the curing temperature for a curing time period in a range 2 minutes to 5 minutes.

20. The method as claimed in claim 1 comprising maintaining the silicone material above the curing temperature for a curing time period in a range 2 minutes to 4 minutes.

* * * * *